United States Patent [19]
Williams

[11] Patent Number: 6,022,308
[45] Date of Patent: Feb. 8, 2000

[54] TUMOR TREATMENT

[75] Inventor: Jeffery A. Williams, Oklahoma City, Okla.

[73] Assignee: Proxima Therapeutics, Inc., Alpharetta, Ga.

[21] Appl. No.: 08/818,966

[22] Filed: Mar. 14, 1997

Related U.S. Application Data

[62] Division of application No. 08/307,165, Sep. 16, 1994, Pat. No. 5,611,767, which is a continuation of application No. 07/715,923, Jun. 14, 1991, Pat. No. 5,429,582.

[51] Int. Cl.⁷ ..................................................... A61N 5/02
[52] U.S. Cl. .................................................................. 600/2
[58] Field of Search ............................................ 600/1–8

[56] References Cited

U.S. PATENT DOCUMENTS

| | | | |
|---|---|---|---|
| 2,043,630 | 6/1936 | Raiche | 18/58 |
| 2,677,375 | 5/1954 | Raiche | 128/349 |
| 3,173,418 | 3/1965 | Baran | 128/351 |
| 3,324,847 | 6/1967 | Zoumboulis | 128/1.2 |
| 3,831,629 | 8/1974 | Mackal et al. | 137/525 |
| 3,872,856 | 3/1975 | Clayton | 128/1.2 |
| 4,022,190 | 5/1977 | Meyer | 128/2 A |
| 4,085,757 | 4/1978 | Pevsner | 604/96 |
| 4,103,689 | 8/1978 | Leighton | 128/350 V |
| 4,133,315 | 1/1979 | Berman et al. | 604/96 |
| 4,206,762 | 6/1980 | Cosman | 128/660 |
| 4,213,461 | 7/1980 | Pevsner | 128/348 |
| 4,281,667 | 8/1981 | Cosman | 128/748 |
| 4,292,960 | 10/1981 | Paglione | 128/1.1 |
| 4,382,445 | 5/1983 | Sommers | 604/8 |
| 4,417,576 | 11/1983 | Baran | 128/207.15 |
| 4,541,429 | 9/1985 | Prosl et al. | 604/249 |
| 4,564,022 | 1/1986 | Rosenfeld et al. | 128/748 |
| 4,588,394 | 5/1986 | Schulte et al. | 604/9 |
| 4,593,703 | 6/1986 | Cosman | 128/748 |
| 4,601,713 | 7/1986 | Fuqua | 604/280 |
| 4,602,655 | 7/1986 | Mackal | 137/515 |
| 4,617,015 | 10/1986 | Foltz | 604/100 |
| 4,619,247 | 10/1986 | Inoue et al. | 128/6 |
| 4,653,508 | 3/1987 | Cosman | 128/748 |
| 4,655,745 | 4/1987 | Corbett | 604/49 |
| 4,655,748 | 4/1987 | Mushika | 601/96 |
| 4,660,568 | 4/1987 | Cosman | 128/748 |
| 4,681,132 | 7/1987 | Lardner | 137/271 |
| 4,681,560 | 7/1987 | Schulte et al. | 604/9 |
| 4,699,615 | 10/1987 | Fischell et al. | 604/131 |
| 4,706,652 | 11/1987 | Horowitz | 128/1.2 |
| 4,710,177 | 12/1987 | Smith et al. | 604/185 |
| 4,754,745 | 7/1988 | Horowitz | 128/1.2 |
| 4,754,752 | 7/1988 | Ginsburg et al. | 128/303.12 |
| 4,763,642 | 8/1988 | Horowitz | 128/1.2 |
| 4,776,369 | 10/1988 | Lardner et al. | 137/515.5 |
| 4,788,063 | 11/1988 | Fisher et al. | 424/449 |
| 4,800,899 | 1/1989 | Elliott | 600/2 |
| 4,816,016 | 3/1989 | Schulte et al. | 604/9 |
| 4,821,725 | 4/1989 | Azam et al. | 128/420 |
| 4,846,191 | 7/1989 | Brockway et al. | 128/748 |
| 4,867,741 | 9/1989 | Portnoy | 604/10 |
| 5,061,475 | 10/1991 | Lieberman et al. | 600/4 |
| 5,061,476 | 10/1991 | Simon et al. | 600/4 |
| 5,084,015 | 1/1992 | Moriuchi | 604/96 |
| 5,106,360 | 4/1992 | Ishiwara et al. | 600/2 |
| 5,112,303 | 5/1992 | Pudenz et al. | 604/49 |
| 5,125,888 | 6/1992 | Howard et al. | 600/12 |
| 5,152,747 | 10/1992 | Olivier | 604/93 |
| 5,236,410 | 8/1993 | Granov et al. | 600/12 |
| 5,300,281 | 4/1994 | McMillan et al. | 600/4 |
| 5,429,582 | 7/1995 | Williams | 600/2 |
| 5,611,767 | 3/1997 | Williams | 600/2 |

FOREIGN PATENT DOCUMENTS

| | | |
|---|---|---|
| 0 205 384 | 12/1986 | European Pat. Off. . |
| 0 340 881 | 11/1989 | European Pat. Off. . |
| 37 25 691 | 3/1988 | Germany . |
| 2 105 201 | 3/1983 | United Kingdom . |
| WO 90 04365 | 5/1990 | WIPO . |
| WO 91 05528 | 5/1991 | WIPO . |
| WO 92 10932 | 7/1992 | WIPO . |
| WO 93 09724 | 5/1993 | WIPO . |

OTHER PUBLICATIONS

Supplementary European Search Report, Application No. 92 91 3085, Dec. 12, 1995.

Garfield et al. (1973) "Postoperative Intracavitary Chemotherapy of Malignant Gliomas"; *J. Neurosurg.* 39:315–322.

(Jun. 1990) *NASA Tech Briefs* p. 106.

Shimm et al.(1988) "Scanned Focused Ultrasound Hyperthermia: Initial Crucial Results" *Int. J. Radiation Oncology Bio. Phys.* 15:1203–1208.

Roberts et al. (1986) "Interstitial Hyperthermia and Iridium Brachytherapy in Treatment of Malignant Gliomas" *J. Neurosurg.* 64.

Chun et al. (1989) "Interstitial iridium–192 Implantation for Malignant Brain Tumours Part II" *The British Journal of Radiology* 62:158–162.

Leibel et al. (1987) Item 13 *Am. J. Clin. Oncol. (CCT)* 10(2):106.

Gutin et al. (1984) "Brahytherapy of Recurrent Malignant Brain Tumors with Removable High–activity Iodine–125 Sources" *J. Neurosurg.* 60:61–68.

Wu et al. (1989) "Interstitial Iridium–192 Implantation for Malignant Brain Tumours Part I" *The British Journal of Radiology* 62:154–157.

(List continued on next page.)

*Primary Examiner*—John P. Lacyk
*Attorney, Agent, or Firm*—Thomas J. Engellenner; Faustino A. Lichauco; Lahive & Cockfield, LLP

[57] ABSTRACT

A completely implantable apparatus is provided for treatment of tissue surrounding a cavity left by surgical removal of a brain tumor. The apparatus includes an inflatable balloon constructed for placement in the cavity. A subcutaneously implantable treatment fluid receptacle is provided for receiving a transdermal injection of a treatment fluid. A catheter connects the receptacle to the inflatable balloon. Various embodiments provide for simultaneous application of heat therapy and/or radiation therapy and/or chemotherapy to the remaining tissue surrounding the cavity from which the tumor was removed.

10 Claims, 4 Drawing Sheets

OTHER PUBLICATIONS

Raaphorst et al. "A Comparison of Heat and Radiation Sensitivity of Three Human Glioma Cell Lines" *J. Radiation Oncology Biol. Phys.* 17:615–622, Sep. 1998.

Exhibit B *Brochure of Halkey–Roberts Corporation of St. Petersburg, Florida* (Undated but admitted to be prior art).

Moidel et al. (1976) "Materials for Selective Tissue Heating in a Radiofrequency Electromagnetic Field for the Combined Chemothermal Treatment of Brain Tumors" *J. Biomed. Mater. Res.* 10:327–334.

TUMOR TREATMENT

This application is a divisional application of Ser. No. 08/307,165 filed on Sep. 16, 1994, now U.S. Pat. No. 5,611,767, which in turn is a continuation application of Ser. No. 07/715,923 filed on Jun. 14, 1991, now U.S. Pat. No. 5,429,582, issued Jul. 4, 1995. The contents of all of the aforementioned application(s) are hereby incorporated by reference.

BACKGROUND OF THE INVENTION

1. Field of the Invention

The present invention relates to apparatus and methods for the treatment of tumors in a living body, and more particularly, but not by way of limitation, to apparatus and methods for treatment of brain tumors in a human.

2. Description of the Prior Art

Conventional techniques of post-operative treatment of residual tumor following only gross removal of tumor include sequential, but not simultaneous administration of radiation, chemotherapy, and/or heat. Simultaneous administration of these modalities to the residual tumor is advantageous but impossible utilizing currently available techniques.

Further, no currently available intraoperative therapeutic procedure utilizes the cavity formerly occupied by the bulk of the tumor for placement of an inflatable device for subsequent tumor therapy, whether combined (radiation and/or chemotherapy and/or hyperthermia together) or single modality (one of the above alone), or whether simultaneous or sequential in application.

The current practice of brachytherapy (implantation of radioactive sources in the tumor and surrounding tissue) requires simultaneous placement of numerous separate catheters. Placement of catheters for afterloading must currently incorporate pre-operative placement of a stereotactic frame for localization, a procedure which is expensive, cumbersome, and time-consuming. In frame placement, a large heavy frame is attached to the skull of the awake patient utilizing transdermal metal screws and local anesthetic, often not a smooth or desirable procedure. Once the frame is placed, a CT scan and extensive calculations are required before the patient is transported to the operating room, with the frame on his or her head, for the actual catheter placements. This second transport is cumbersome.

Once in the operating room, numerous separate holes (usually up to 24) are manually drilled in the patient's scalp and skull. Then existing catheters are placed to the appropriate depth and sewn into place. These catheters are subsequently afterloaded with solid isotopic pellets for a prescribed time. The pellets are removed and, if hyperthermia is desired, separate metal antennae are loaded into the existing catheters for subsequent heating and thermometry. Although reasonably proximal in time, these sequential loadings reduce the efficacy of combined treatment, which should be simultaneous for highest tumor kill. During treatment, the catheters are externally exposed with attendant risk of infection.

Following delivery of the prescribed radiation and heat, the catheters are removed. Any subsequent treatment, as for example following tumor recurrence, would require repeating the entire sequence described above.

SUMMARY OF THE INVENTION

For these reasons, it would be desirable to provide methods and apparatus for intial intra-operative placement of a completly implantable device for sebsequent simultaneous hyperthermia and/or radiation and/or chemotherapy treatment for brain tumors or tumors in other sites. Just such a system is provided by the present invention.

An implantable apparatus is provided for treatment of tissue surrounding a cavity left by surgical removal of a tumor from a living patient. The apparatus includes an inflatable balloon constructed for placement in the cavity. A treatment fluid receptacle means is provided for receiving a transdermal injection of a treatment fluid. A catheter means is connected between the receptacle means and the balloon for carrying the treatment fluid from the receptacle means to the inflatable balloon.

The treatment fluid can be a radioactive treatment fluid or a chemotherapy fluid, or in one embodiment a double-wall balloon is provided so that both a radioactive treatment fluid and a chemotherapy fluid can be simultaneously applied.

Various means are provided for heating the treatment fluids thus also providing the alternative of simultaneous heat therapy.

Monitoring means are provided for monitoring the temperature of the treatment fluid in the balloon.

The invention provides a significant advantage in that it provides a means for simultaneous administration of radiation therapy and/or chemotherapy and/or heat therapy.

Another advantage is that a treatment device is intraoperatively placed in the cavity formerly occupied by the bulk of the tumor thus providing a means for subsequent treatment of residual tumor without further surgical incisions.

Another advantage is that the distensible balloon takes advantage of the inherent natural compliance of a fluid to conform to the outline of the cavity to be treated, thus allowing close approximation of the treatment device to the treated residual tumor.

The present invention also takes advantage of the greater variety of desirable physical or superior cost properties inherent in readily available liquid isotopes. These liquid isotopes are cheaper and possess higher specific activities (millicuries per gram) when compared to their conventional, solid counterparts. This is a highly desirable characteristic which allows a higher concentration of radioactivity to be administered, thus resulting in higher tumor cell kill.

Another advantage of the present invention is that it allows homogeneous mixing of disparate treatment agents for the uniform administration of hyperthermia and brachytherapy simultaneously to a human tumor surrounding a post-operative cavity.

Numerous other objects, features and advantages of the present invention will be readily apparent to those skilled in the art upon a reading of the following disclosure when taken in conjunction with the accompanying drawings.

BRIEF DESCRIPTION OF THE DRAWINGS

FIGS. 1–4 comprise a sequential series of schematic elevation sectioned drawings through the coronal portion of the head of a human being.

DETAILED DESCRIPTION OF THE PREFERRED EMBODIMENTS

Figure 1:
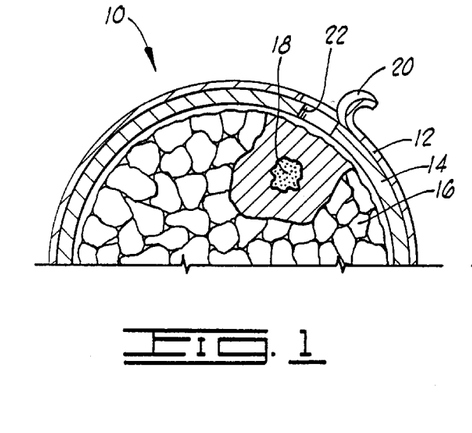
In FIG. 1 the scalp has been laid back and one or more burr holes are placed in the skull allowing creation of a circular bone flap which when temporarily removed allows gross resection of the tumor.

In FIG. 1 the coronal portion of the head of a human patient is shown and generally designated by the numeral 10. The patient's scalp 12 overlies the skull 14 within which is seen the brain 16. A tumor 18 is schematically illustrated within the brain tissue 16. The scalp 12 has been laid back as indicated at 20 and one or more burr holes have been cut to allow creation of a bone flap (not shown) which is removed to form an access opening 22 in the skull thus providing operative access to the brain 16 and the tumor 18.

Figure 2:
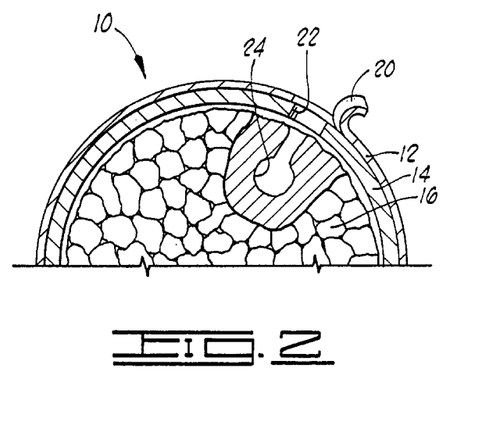
In FIG. 2 the major portion of a brain tumor has been operatively removed.

In FIG. 2, the bulk of the tumor 18 has been operatively removed thus leaving a cavity 24 within the remaining brain tissue 16 which will include some residual tumor immediately surrounding the cavity 24.

Figure 3:
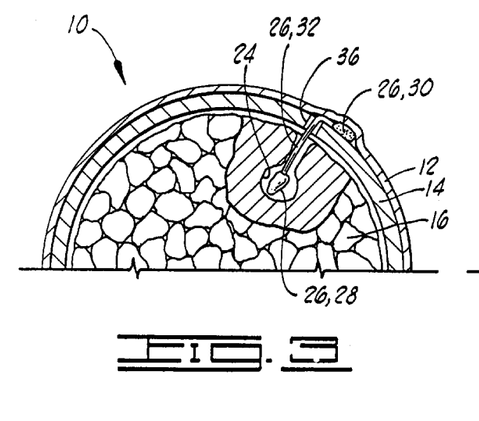
In FIG. 3 intra-operative placement of the implantable apparatus of the present invention has been accomplished and the incision has been closed.

In FIG. 3, the implantable treatment apparatus 26 has been intra-operatively implanted prior to closure of the surgical incisions. The apparatus 26, as better seen in FIG. 5, includes an inflatable balloon 28 constructed for placement in the cavity 24, a subcutaneously implantable treatment fluid receptacle means 30, and a catheter means 32 connected between the receptacle means 30 and the balloon 28 for carrying treatment fluid from the receptacle means 30 to the inflatable balloon 28.

The assembly of the implanatable apparatus 26 is generally as follows starting with the subcutaneous receptacle 30 and moving distally. The various connections discussed in the following description are not shown in detail in the figures, but comprise conventional widely acceptable neurosurgical techniques and will be well understood by those skilled in the art. An outlet connector extends outwardly from the subcutaneous receptacle 30 and engages an end of the siliconized plastic surgical tubing comprising the catheter 32 in a manner like that shown in FIG. 7 of U.S. Pat. No. 4,681,560 to Schulte et al., the details of which are incorporated herein by reference. The end of the outlet connector from the subcutaneous receptacle 30 includes a flange portion which sealingly engages a suture sleeve to form a seal preventing medication from exiting the assembly other than through the connector leading to the catheter 32.

Figure 5:
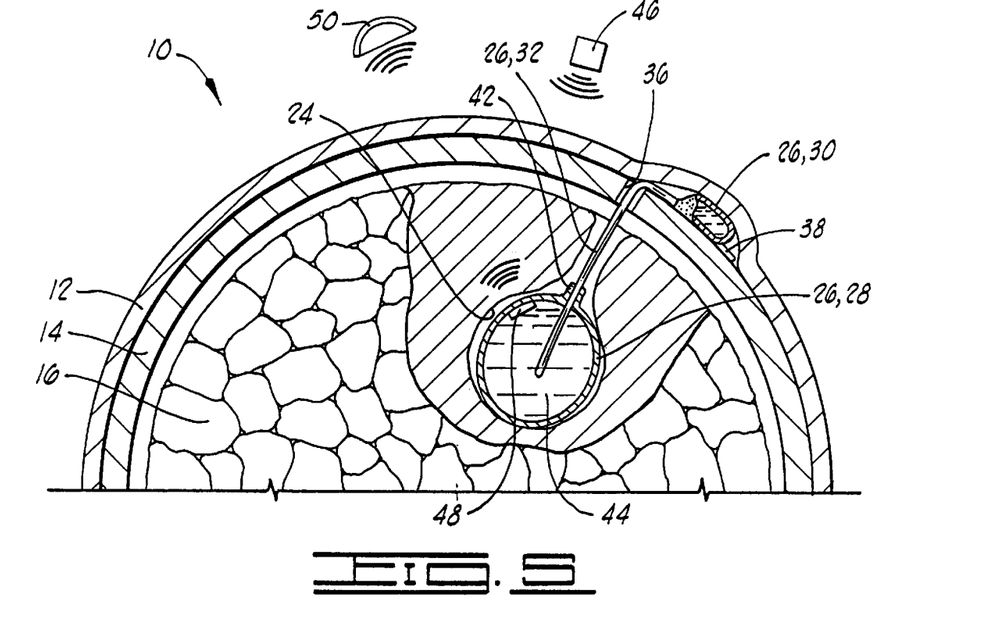
FIG. 5 is an enlarged view similar to FIG. 4 illustrating further details of the apparatus including means for heating and means for monitoring the temperature of the fluid in the balloon.

In order for the catheter 32 to make the right-angle turn downward through burr hole 36 as illustrated in FIG. 5, a plastic right-angle device (not shown) which causes the catheter tube 32 to be conformed to a right angle can be placed around the tube at the time of installation at the proper linear dimension along the tube. Thus, depending upon the necessary distance between the subcutaneous receptacle 30 and the burr hole 36, the right-angle device may be located closer to or further from the subcutaneous receptacle 30. These assembly techniques just described confer considerable flexibility in the placement and installation of the various components of the treatment device 26.

In FIG. 3, the apparatus 26 has been implanted with the balloon 28 located within cavity 24 but still in its uninflated state. The access opening 22 has been closed by replacement of the previously removed bone flap. The catheter means 32 is placed through a burr hole 36 which may have been formed when the bone flap was formed, or which may be specially formed in any desired location. The subcutaneous receptacle 30 has been placed on top of the skull 14 and the scalp 12 has been sutured back in place thereover. The receptacle 30 may include a suture tab such as 38 (see FIG. 5) allowing it to be sutured in place to the surrounding galea which is a tough overlying tissue which lies over the skull 14.

Figure 4:
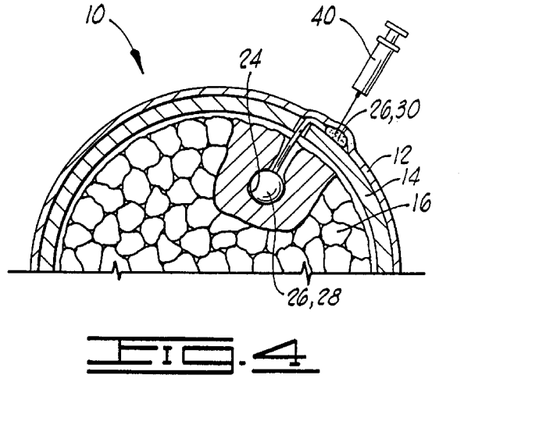
In FIG. 4 a hypodermic needle is used to transdermally place a treatment fluid in the apparatus to inflate the distensible catheter in place within the cavity formed by removal of the tumor.

In FIG. 4 a hypodermic needle 40 is illustrated as transdermally injecting a treatment fluid into the subcutaneously implanted receptacle 30. The injection receptacle 30 includes a rigid base and an overlying self-sealing dome which encloses and defines an injection chamber. The self-sealing dome is constructed of a silicone elastomer material, such materials providing an acceptable level of tissue reaction when subcutaneously implanted, which can be pierced by a 25 gauge or smaller needle without affecting ability of the dome to reseal after the needle is withdrawn. The fluid from needle 40 flows through the catheter 32 to inflate the balloon 28 so that it substantially fills the cavity 24 thus placing the treatment fluid in close proximity to the remaining tumor in the brain tissue 16 surrounding the cavity 24. The walls of balloon 28 can generally be described as being in direct apposition with the remaining residual tumor tissue surrounding cavity 24. As further described below, various treatment modalities may be applied either individually or simultaneously.

The Embodiment Of FIG. 5

FIG. 5 illustrates the apparatus 26 in a view similar to that of FIG. 4 but enlarged and showing further detail.

The subcutaneously implanted receptacle means 30 is constructed in a manner so that it can be easily and safely injected with the treatment fluid, and it is constructed of a material which will readily reseal upon withdrawal of the hypodermic needle. It may for example be constructed similarly to the subcutaneously implantable infusion reservoir shown and described in Schulte et al., U.S. Pat. Nos. 4,816,016 and 4,681,560, the details of which are incorporated herein by reference. It may also be an Ommaya CSF Reservoir such as is available from American Heyer-Schulte. The design of the subcutaneously implantable reservoir 30 should be small enough to minimize the volume of radioactive treatment fluid 44 in the subcutaneous area, but should be large enough to allow easy localization by palpation to facilitate loading with the hypodermic syringe 40. The subcutaneous receptacle 30 should be malleable and flexible to allow external palpation, but should be rigid enough that external compression cannot drive fluid from its interior into the catheter 32 and balloon 28. If compression should occur, the resilience of subcutaneous receptacle 30 should provide for re-expansion, thus re-accumulating any fluid driven distally as noted above.

The catheter means 32 is constructed of conventional flexible plastic catheter materials.

The inflatable balloon 28, which may also be referred to as a distensible reservoir 28 or distensible catheter 28, is preferably constructed of flexible siliconized plastic and is attached to the catheter means 32 at location 42 by a flanged plastic connector and multiple interrupted surgical ties.

Although the term "balloon" is used to describe the distensible reservoir 28, it will be appreciated that the material from which the balloon wall is constructed need not be an elastic material. It is only required that the reservoir 28 be capable of somewhat collapsing in size so that it can be easily placed in cavity 24 as shown in FIG. 3 and that it then subsequently fill with fluid so as to substantially fill the cavity 24. The fluid inside balloon 28 is not necessarily pressurized, although it may be. The collapse of the balloon 28 following treatment will allow easy removal of the catheter 32 and balloon 28 through an existing burr hole 36 without first removing the entire bone flap should removal of the device be required for any reason.

In one preferred embodiment the treatment fluid 44 is a radioactive treatment fluid. The radioactive treatment fluid can be injected into the balloon 28 and left there for a prescribed period of time. Then it may be removed by reinserting hypodermic needle 40 into receptacle 30 and pulling a vacuum with the plunger of hypodermic needle 30 to cause the treatment fluid to flow back out of balloon 28 through catheter 32 into receptacle 30 and into the cylinder of hypodermic needle 40, so as to end the radiation treatment. Preferred radioactive isotopes for use in this procedure include 90-Yttrium, 198-Gold, 32-Phosphorous, 125-Iodine and 131-Iodine. The use of isotopes in liquid form allows considerable flexibility in administered dose rate in rad/hour and range (in millimeters) of the radioactive particles used in irradiating the residual tumor. Also with this apparatus a much more homogeneous dosage of radiation is applied to the surrounding tissue 16 than with the typical prior art devices described.

It is noted that since the apparatus 26 can be loaded with radioactive solution after the completion of surgery there is much less danger of radiation exposure to operating room personnel than with the prior art techniques described above.

Of course for treatment with radioactive fluid 44, the balloon 24 would be made of non-porous material. For other treatment modalities, namely chemotherapy, a balloon 28 constructed of porous material may be utilized in a manner similar to that described below with regard to the porous outer wall 28A of FIG. 7, in order to allow the chemotherapy fluids to seep through the balloon 28 into actual contact with the surrounding brain tissue. When a porous balloon wall 28 is used for chemotherapy, so that there is no need to ever withdraw the treatment fluid from the balloon 28, the treatment device 26 may further include a check valve (not shown) disposed in catheter 32 similar to valve 82 of FIG. 7 so that fluid can flow to balloon 28 but not back therefrom.

It is noted that the inflatable balloon 28 is preferably constructed so that it has an inflated volume as seen in FIG. 5 which is no greater than, and preferably slightly less than, the volume of the cavity 24 thus providing a means for avoiding any compression or distortion of the normal brain tissue 16 surrounding the cavity 24. It will be appreciated, of course, that distortion of the normal brain tissue can cause undesired complications.

FIG. 5 also illustrates a first form of heating means 46 operatively associated with the balloon means 28 for non-invasive heating of the treatment fluid 44 while the treatment fluid 44 is in the balloon 28. The heating means 46 illustrated in FIG. 5 may either be an external ultrasonic transmission means 46 or an external radio frequency electromagnetic energy transmission means 46.

If the heating means 46 is an external ultrasonic transmission means, it focuses ultrasonic energy on the treatment fluid 44 in balloon 28. In the case of using ultrasonic energy to heat the balloon contents, the skull bone tissue 14 will not be replaced over the burr hole 22 thus providing a path for unimpeded transmission of the ultrasonic sound energy through the burr hole 22.

If the heating means 46 is an external radio frequency electromagnetic energy transmission means, the treatment fluid 44 will contain an iron oxide suspension in addition to the radioactive isotope in solution. This iron oxide suspension will be heated by the radio frequency electromagnetic energy.

A monitoring means 48 is provided for monitoring a temperature of the treatment fluid 44 within the balloon means 28. In a preferred embodiment, the monitoring means 48 is a crystal oscillator 48 implanted within the balloon means 28. The oscillator 48 may also be mounted on the outside of catheter 32 within balloon 28. The crystal oscillator 48 has a frequency of oscillation which varies proportionately to its temperature. The frequency of oscillation of the crystal oscillator means 48 can be determined non-invasively by an external antenna 50 which may be considered to be a part of the monitoring means. The crystal oscillator 48 is available under the trade name CorTemp from Human Technologies, Inc., of St. Petersburg, Fla., such as described in "NASA Tech Briefs", June, 1990, at page 106, the details of which are incorporated herein by reference.

The system shown in FIG. 5, when using a non-porous balloon 28, provides a means for simultaneous application of both radioactive therapy and heat therapy to the remaining brain tissue 16 surrounding the cavity 24.

In its broadest aspects, the surgical procedure utilizing the apparatus of FIG. 5 can be described as including steps of surgically removing at least a portion of the tumor 18 thereby creating the cavity 24 in the remaining brain tissue 16. Subsequently the treatment device 26, 28 is placed in the cavity 24 and the remaining tissue 16 including residual tumor surrounding the cavity 24 is treated by means of the treatment device 26, 28. The treatment device 28 preferably is an inflatable balloon 28. The inflatable balloon is inflated with a treatment fluid 44 so that the inflatable device 28 occupies the cavity 24 thereby placing the treatment fluid 44 in close proximity to the remaining tissue 16 surrounding the cavity 24. By use of the subcutaneously implanted receptacle 30 and transdermal injections of treatment fluid as indicated in FIG. 4, the procedure can be performed non-invasively without making further surgical incisions on the patient. Although the apparatus and process of the present invention have been disclosed in the context of treatment of brain tumors, it will be appreciated that they can be used in connection with other types of tumors wherein treatment can be accomplished by placing the treatment device in a cavity left by removal of the tumor.

The entire apparatus 26 can be left in place permanently allowing subsequent further treatment as desired.

Figure 6:
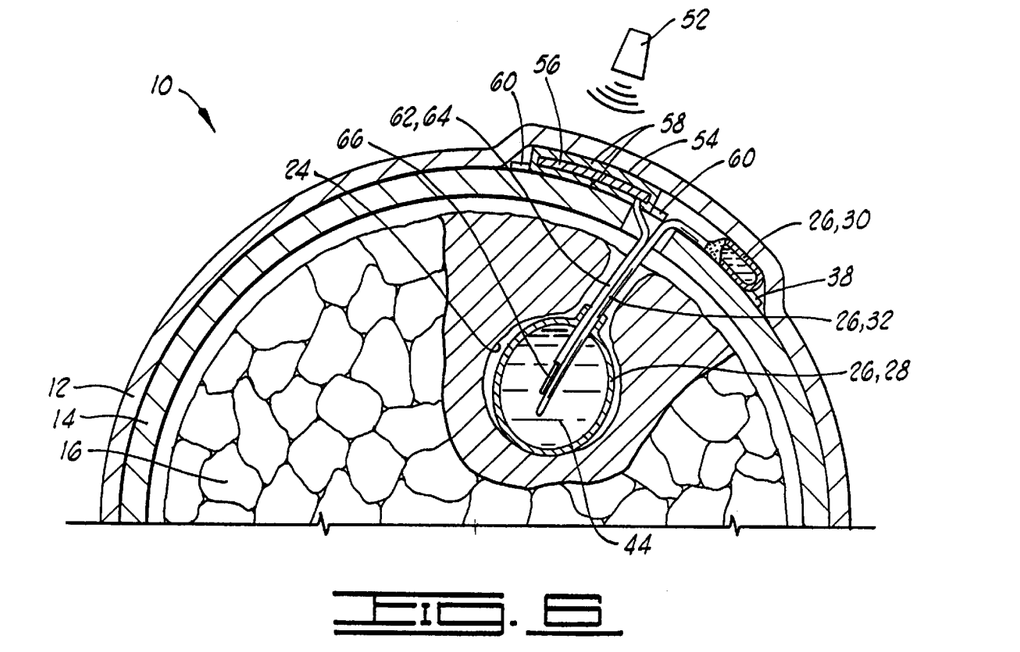
FIG. 6 is a view similar to FIG. 5 illustrating alternative means for heating.

The Embodiment Of FIG. 6

FIG. 6 illustrates an alternative embodiment providing a different means for heating the treatment fluid 44 within the balloon 28.

The system shown in FIG. 6 utilizes an external microwave transmitter 52, and a subcutaneously implantable microwave receiver means 54. The microwave transmitter 52 preferably operates in the 200 MHz to 400 MHz range, and more preferably operates at about 300 MHz. The microwave receiver means 54 includes a metallic element 56 which actually receives the microwave energy and heats up. The microwave transmitter 52 may also be replaced by an ultrasound transmitter focused on received means 54. Insulation 58 both overlies and underlies the metallic element 56 to prevent heating of the scalp 12 and underlying skull tissue 14. Suture tabs 60 may be used to attach the microwave receiver apparatus 54 to the skull 14.

A conductor means 62 extends from the metallic element 56 into the interior of the balloon 28 for conducting heat from the metallic element 56 into the treatment fluid 44 in the balloon 28. The conductor means 62 has external insulation 64 which covers a metallic conductor 66 a portion of which is uncovered inside of the balloon 28. Alternatively, the conductor means 62 could be run through the hollow catheter 32.

The system of FIG. 6 may also use a temperature monitoring means 48, 50 as shown in FIG. 5.

Figure 7:
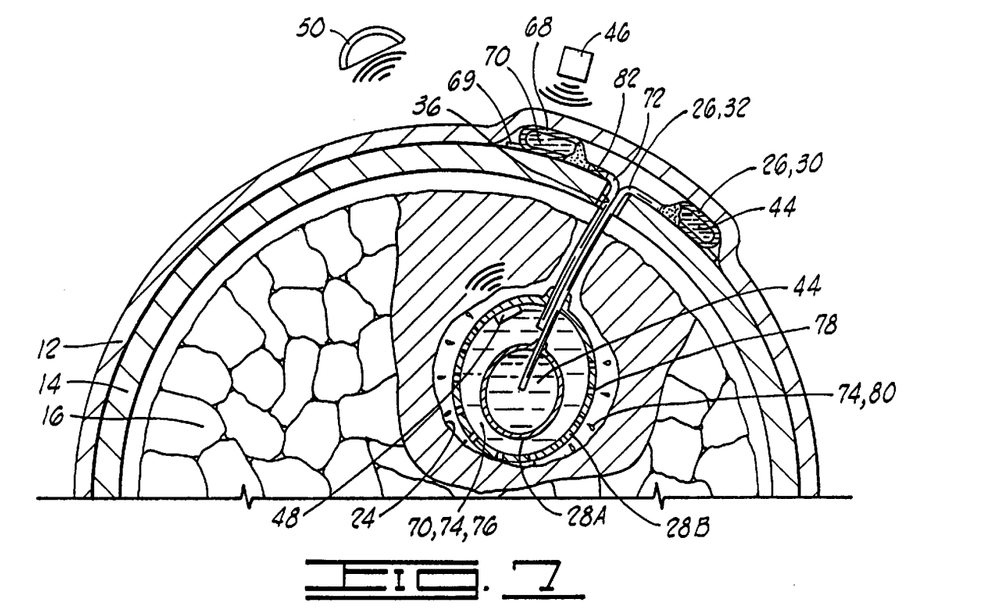
FIG. 7 is a view similar to FIG. 5 illustrating an alternative embodiment of the invention having a double-wall balloon to allow chemotherapy treatments.

The Embodiment Of FIG. 7

FIG. 7 shows another alternative embodiment of the invention wherein the balloon is a double-wall balloon having a non-porous inner wall 28A, and a porous outer wall 28B. The first. subcutaneously implantable receptacle 30 and catheter 32 previously described communicate with the non-porous inner wall 28A for providing the first treatment fluid 44 to the interior of the inner wall 28A. The first treatment fluid 44 is preferably a radioactive treatment fluid. The heating means 46 previously described is provided for non-invasive heating of the first treatment fluid 44. The alternative heating means of FIG. 6 could also be utilized.

A second subcutaneously implantable receptacle means 68 is provided for receiving a transdermal injection of a second treatment fluid 70, which preferably is a chemotherapy treatment fluid 70. The second receptacle 68 may be held in place by suture tabs such as 69. A second catheter 72 communicates the second receptacle 68 with the space 74 defined between the inner and outer walls 28A and 28B within which the chemotherapy fluid 70 is received. The space 74 preferably has a layer of sponge-like material 76 lying therein between the inner and outer walls 28A and 28B for temporarily holding the chemotherapy fluid 74 therein.

The porous outer wall 28B includes numerous small openings 78 therein allowing the chemotherapy fluid 74 to seep out such as in droplets 80. The chemotherapy fluid seeps out the porous outer wall 28 into direct contact with the brain tissue 16 surrounding the cavity 24.

The previously described crystal oscillator 48 may be placed within either the inner wall 28A or within the outer wall 28B for monitoring of the temperature of the fluids therein as previously described.

A check valve 82 may be disposed in the second catheter 72 for preventing flow of the chemotherapy fluid 70 back therethrough from space 74 back to receptacle 68. The one-way check valve 82 is available from Halkey-Roberts Corporation of St. Petersburg, Fla., and may for example be constructed in accordance with the teachings of U.S. Pat. No. 4,681,132 to Lardner, the details of which are incorporated herein by reference.

It will be appreciated that fluid pressures both from the first fluid 44 within the inner wall 28 and the second fluid 70 within the space 74 will act to urge the second fluid 70 out through the small openings 78 in the porous outer wall 28B.

FIG. 7 illustrates a treatment means including heating means 46 and the first and second subcutaneous receptacles 30 and 68 operably associated with the balloon means 28A, 28B for simultaneously non-invasively applying at least two, and if preferred all three, treatment modalities from the group consisting of radiation, heat and chemotherapy to remaining brain tissue 16 surrounding the cavity 24.

Alternatively, instead of use of a double-wall balloon 28A, 28B, chemotherapy alone could be applied with a structure like that shown in FIG. 5 wherein the outer wall 28 is a porous wall and wherein the interior thereof contains a sponge-like material.

Figure 8:
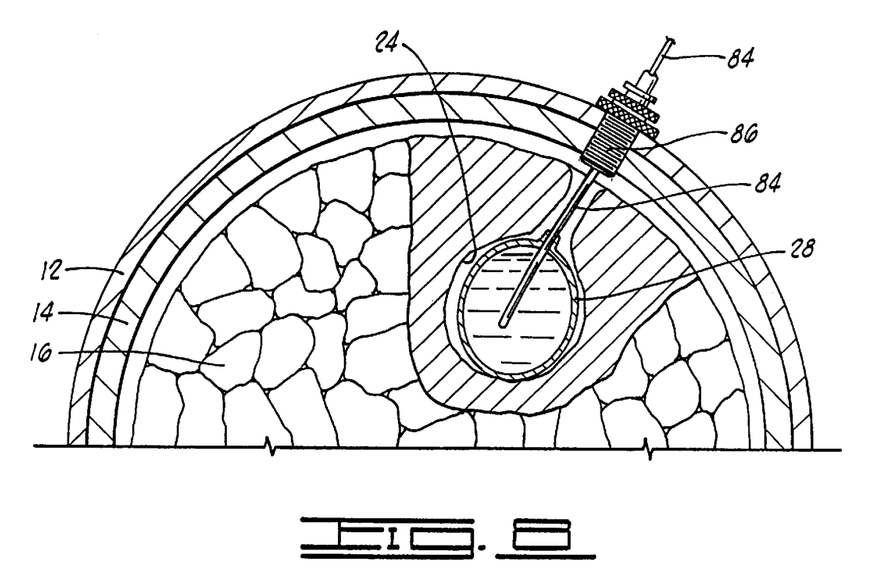
FIG. 8 is a view similar to FIG. 5 of another alternative embodiment which is not completely implantable, and which has the catheter extending through a bolt means placed in the skull.

The Embodiment Of FIG. 8

FIG. 8 illustrates a balloon 28 like that of FIG. 5, and also illustrates the fact that certain aspects of the present invention can be achieved without the use of the subcutaneously implanted receptacle 30, but instead by having a transdermal catheter 84 extend through the skull 14 and scalp 12 by means of a hollow bolt 86 implanted in the skull 14 which has the transdermal catheter 84 sealingly and securely disposed therethrough. The hollow bolt 86 may if desired be made of non-metallic materials.

Figure 9:
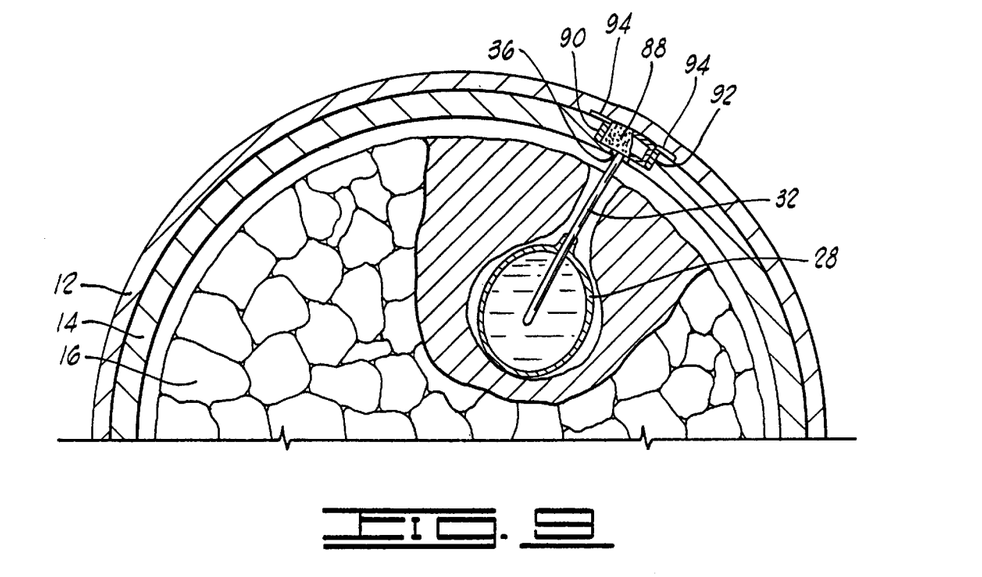
FIG. 9 is a view similar to FIG. 5 of another alternative embodiment having a treatment fluid receptacle countersunk within the skull so as to avoid deformation of the overlying scalp. The implantable receptacle includes a metallic ring which is visible to X-rays.
Figure 10:
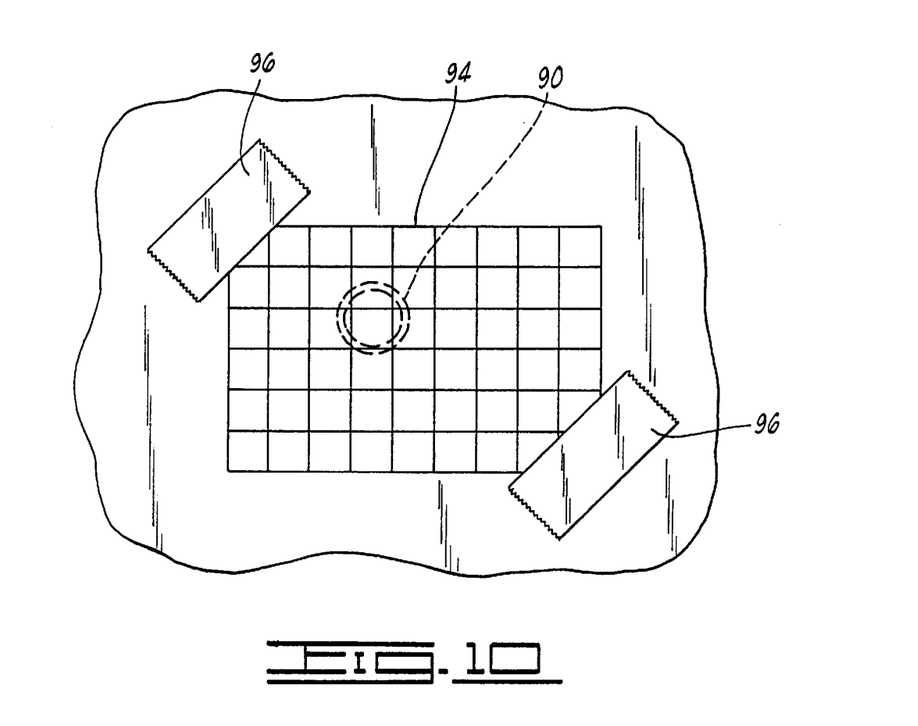
FIG. 10 schematically illustrates the placement of a metallic wire grid over the patient's scalp, with the metallic ring of the device of FIG. 9 being shown in dashed lines as it would be seen in a subsequent en face X-ray of the patient's scalp for purposes of locating the receptacle.

The Embodiment Of FIGS. 9 And 10

FIGS. 9 and 10 illustrate another embodiment of the invention. In FIG. 9 a modified subcutaneously implantable receptacle 88 is illustrated. It is connected to balloon 28 by catheter 32.

It will be appreciated that the subcutaneously implantable reservoir 30 shown in FIGS. 1–7 is designed such that the overlying scalp 12 is somewhat deformed to accommodate the size of the subcutaneous receptacle 30. The subcutaneous receptacle 30 of FIGS. 1–7 is typically located by palpation of the scalp 40 so as to locate the subcutaneous reservoir 30 by feel. It will be appreciated that a palpable receptacle such as receptacle 30 implies pressure upon the overlying scalp 12 which may compromise blood supplied to the scalp 12 in that area, hence potentially causing skin necrosis or breakdown, a definite disadvantage.

The modified receptacle 88 is circular in shape and includes an annular metallic ring 90 which is impenetrable by X-rays. The receptacle 88 and metallic ring 90 are placed within a counterbore 92 which is formed within the skull 14 with commonly utilized air-driven drills such as that manufactured by the Midas Rex Company. The receptacle 88 may be held in place by suture tabs 94. It may also be held in place by conventional threaded screws (not shown) screwed into the skull 14.

The modified receptacle 88 may be installed in such a manner so as not to deform the overlying scalp 12 or create undue pressure upon the scalp 12. It does, however, present a need for an easy means of accurately locating the subcutaneous receptacle 88 so that treatment fluids may be injected therein with a hypodermic 40 similar to the process illustrated in FIG. 4. This localization is accomplished as shown in FIG. 10.

A metallic grid 94 is laid in place over the patient's scalp 12 and may be held fixedly in place thereon by means such as tape 96. Next, a plain en face radiograph, i.e., X-ray, of scalp, reservoir, grid and skull is taken. By observing the X-ray film, the relationship between the external metallic grid 94 and the subcutaneous metallic ring 90 may be easily seen, allowing selection of the correct grid square externally through which the hypodermic needle 40 can be successfully passed to hit the center of the subcutaneous receptacle 88.

Thus it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art which changes are encompassed within the scope and spirit of the present invention as defined by the appended claims.

What is claimed is:

1. A treatment fluid for treatment of a tumor in a patient, comprising:
   a carrier fluid;
   a ferromagnetic material; and
   a radioactive material, said ferromagnetic material and said radioactive material being mixed together in said carrier fluid,
   wherein said ferromagnetic material is present in an amount effective to heat said treatment fluid in response to radio frequency electromagnetic energy.

2. The treatment fluid of claim 1, wherein said ferromagnetic material is iron oxide.

3. The treatment fluid of claim 1, wherein said radioactive material is in solution in said carrier fluid.

4. The treatment fluid of claim 1, wherein said radioactive material comprises a radioisotope selected from the group consisting of 90-Yttrium, 198-Gold, 32-Phosphorus, 125-Iodine, and 131-Iodine.

5. A treatment fluid for treatment of a tumor in a patient, comprising:
   a carrier fluid;
   a ferromagnetic material; and
   a radioactive material;
   said ferromagnetic material and said radioactive material being mixed together in said carrier fluid,
   wherein said radioactive material is in solution in said carrier fluid.

6. A method for providing simultaneous heat treatment and radiation treatment of a tumor in a living patient, the method comprising:
   placing an inflatable treatment device in a cavity adjacent the tumor;
   inflating the inflatable treatment device with a treatment fluid comprising a carrier fluid, a ferromagnetic material, and a radioactive material; and
   applying radio frequency electromagnetic energy to the treatment fluid, such that the treatment fluid is heated and simultaneous heat treatment and radiation treatment of the tumor is provided.

7. The method of claim 6, wherein the method comprises, prior to the placing step, the step of surgically removing at least a portion of the tumor, thereby creating a cavity in the patient's remaining tissue.

8. The method of claim 6, wherein said ferromagnetic material and said radioactive material are mixed together in said carrier fluid, and said radioactive material is in solution in said carrier fluid.

9. The method of claim 6, wherein the ferromagnetic material is iron oxide.

10. The method of claim 6, wherein the radioactive material comprises a radioisotope selected from the group consisting of 90-Yttrium, 198-Gold, 32-Phosphorus, 125-Iodine, and 131-Iodine.

* * * * *